May 17, 1949 J. D. SIEBENTHALER Plant Pat. 836

HONEY LOCUST TREE

Filed Oct. 14, 1947 2 Sheets-Sheet 1

Inventor
J. D. Siebenthaler
By Robb & Robb
Attorneys

HONEY LOCUST TREE

Filed Oct. 14, 1947 2 Sheets-Sheet 2

Inventor
J. D. Siebenthaler
By Robb & Robb
attorneys

Patented May 17, 1949

Plant Pat. 836

UNITED STATES PATENT OFFICE

836

HONEY LOCUST TREE

John D. Siebenthaler, Dayton, Ohio, assignor to The Siebenthaler Co., Dayton, Ohio, a corporation of Ohio Application October 14, 1947, Serial No. 779,796

1 Claim. (Cl. 47—59)

The present invention or discovery relates to a new and distinct variety of honey locust tree originating by selection from seedlings of the variety *Gleditsia triacanthos* inermis.

It is well known that locust trees are generally very valuable for park planting and for street ornamentals because of their shade characteristics. The type from which the present variety springs is quite common in certain sections of this country, but due to the thorns and/or seed production of most of them, the desirability of use of the honey locust on streets for shade purposes has been practically out of the question, especially in close proximity to heavy traffic and/or where it is desirable to grow grass or other crops under trees.

The discovery and development of the new variety described herein from the standpoint of three of its characteristics is commercially important, under such conditions, said characteristics being habit of growth, its thornlessness and absence of fruit. While other thornless instances are not uncommon, it is to be understood that the value of the present variety lies not only in the combination of its thornless and fruitless traits, but also in the facts that the new variety develops into a large tree of desirable vase-shaped top, grows faster than average, and has darker green leaves as compared to the seedling type from which it comes, which vary greatly in size, shape, rate of growth, color of foliage, fruiting and thorn production.

The tree here described has been developed to maturity to make sure it will never develop fruit and to determine whether the characteristics above referred to were fixed in its progeny. It may be noted in this connection that other locust trees in the same location, planted at the same time, have been fruiting regularly, showing clearly that a mutation has occurred.

Figure 1:
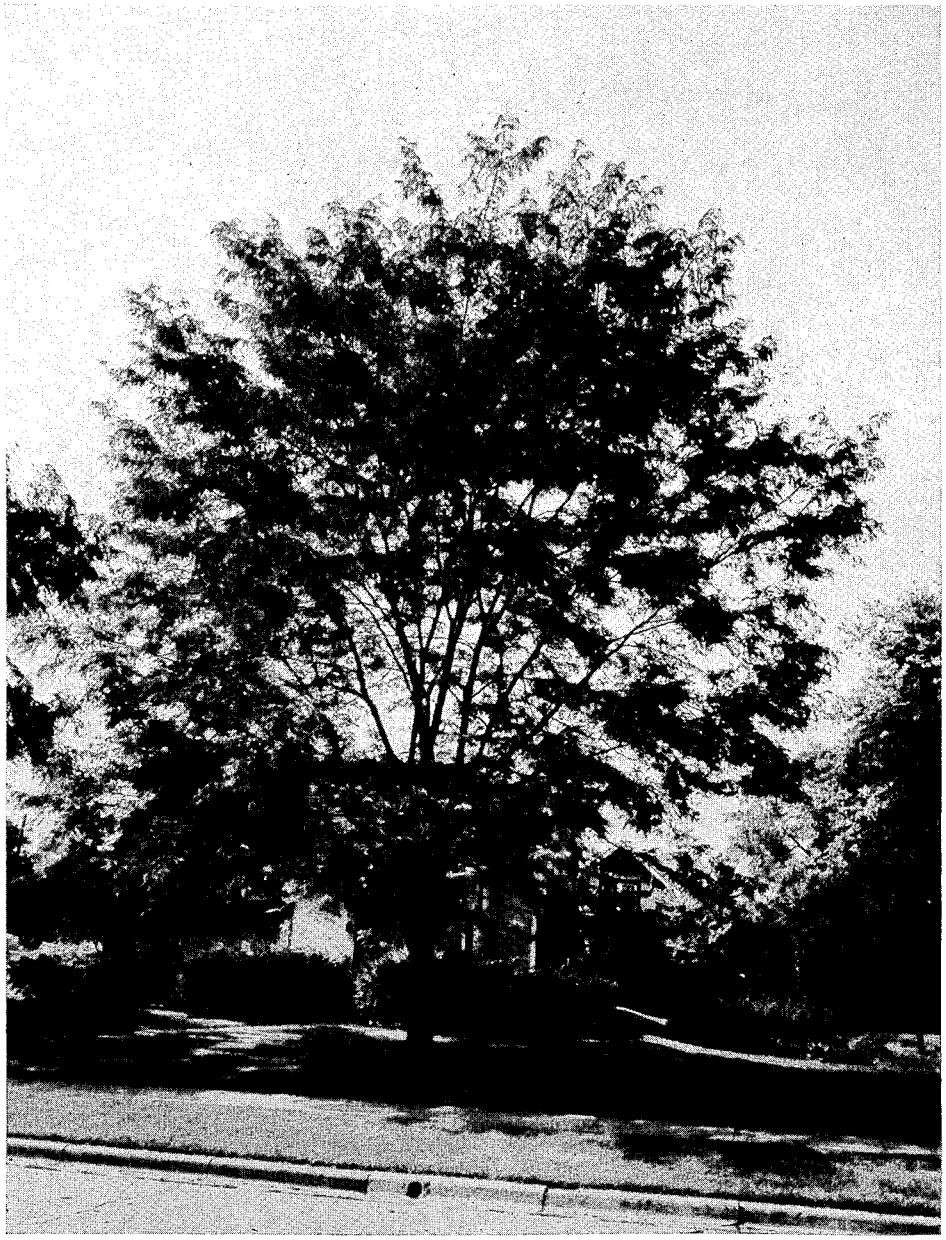
Figure 2:
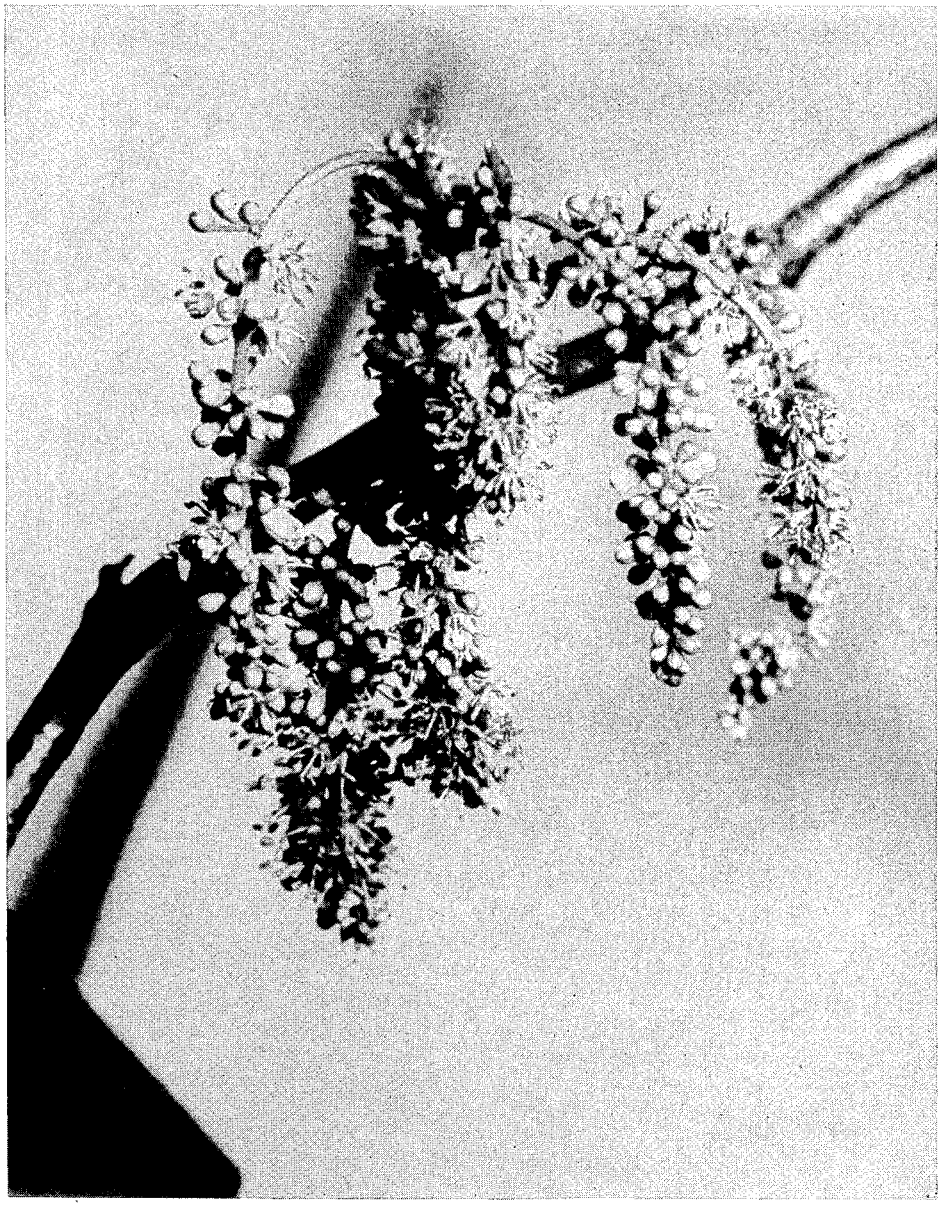

In the accompanying drawings:

Fig. 1 is a view in elevation of a specimen of this new locust, showing its dense foliage for shade purposes, and its uniform symmetrical shape; and Fig. 2 is an enlarged illustration of a specimen of the flowers of this variety showing one of the main features of novelty. To one skilled in the art, it will be apparent that these are only male flowers, there being no female organs present or produced by the flowers of this tree.

The following is a detailed description of the new variety, color terminology being in accordance with ordinary dictionary significance:

Specimens described grown at Dayton, Ohio.

Tree: Large; vigorous; spreading; open, but denser than the prior honey locust of the class from which this originated; vase-formed; round topped when young, developing into vase shape as upper branches exceed lower branches in length; hardy; unproductive; thornless; progeny also thornless.

Trunk: Medium; smooth.

Branches: Diffuse, ascending and outward curving, forming broad vase-shaped head; medium; smooth; brown; glossy.

Leaves: Pinnate and/or bipinnate; length 8″ to 12″; width 4″ to 8″; large; leaflets 20 to 30, length 1″ to 1½″, width ½″; oblong lanceolate; abruptly pointed; medium thick; dark green; smooth.

Margin: Crenulate serrate.

Petiole: Short; slender.

Flowers: Male flowers only.

Fruit: None.

Use: As street tree, shade and lawn tree.

I claim:

A new and distinct variety of honey locust tree, characterized as to novelty by its habit of quick growth, its size and shape, its dense foliage suitable for shade purposes, its fruitlessness and consequent lack of production of seed pods, and the absence of thorns, substantially as shown and described.

JOHN D. SIEBENTHALER.

No references cited.